United States Patent
Schelberger et al.

[11] Patent Number: 6,090,835
[45] Date of Patent: Jul. 18, 2000

[54] FUNGICIDAL MIXTURES

[75] Inventors: Klaus Schelberger, Gönnheim; Maria Scherer, Landau-Godramstein; Hubert Sauter, Mannheim; Manfred Hampel, Neustadt-Hambach; Joachim Leyendecker, Ladenburg; Eberhard Ammermann, Heppenheim; Gisela Lorenz, Neustadt; Siegfried Strathmann, Limburgerhof, all of Germany; Peter Irwin, Cary; Randall Evan Gold, Apex, both of N.C.

[73] Assignee: BASF Aktiengesellschaft, Ludwigschafen, Germany

[21] Appl. No.: 09/151,810

[22] Filed: Sep. 14, 1998

Related U.S. Application Data

[62] Division of application No. 08/870,361, Jun. 6, 1997, abandoned.

[51] Int. Cl.⁷ .......... A01N 43/38; A01N 43/50; A01N 43/56; A01N 43/76
[52] U.S. Cl. .......... 514/376; 514/391; 514/407; 514/421
[58] Field of Search .................. 514/376, 407, 514/391, 421

[56] References Cited

FOREIGN PATENT DOCUMENTS 9601256  1/1996  WIPO.

*Primary Examiner*—Allen J. Robinson
*Attorney, Agent, or Firm*—Keil & Weinkauf

[57] ABSTRACT

Fungicidal mixtures, comprising
a.1) a phenyl-benzylether of the formula I.a, I.b or I.c,

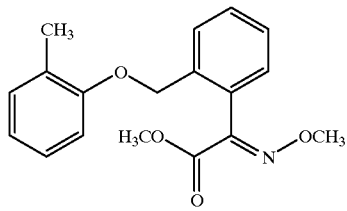

I.a

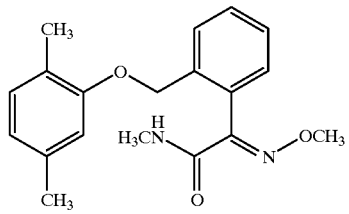

I.b

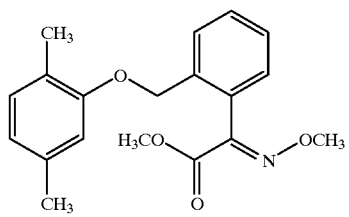

I.c or a.1) a carbamate of the formula I.d,

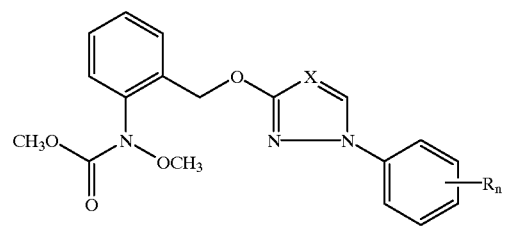

I.d where X is CH and N, n is 0, 1 or 2 and R is halogen, $C_1$–$C_4$-alkyl and $C_1$–$C_4$-haloalkyl, it being possible for the radicals R to be different when n is 2, and b) a dicarboximide-type fungicide (II)

in a synergistically active amount.

13 Claims, No Drawings

FUNGICIDAL MIXTURES

This is a Divisional Application of application Ser. No. 08/870,361, filed on Jun. 6, 1997, abandoned.

The present invention relates to a fungicidal mixture which comprises a.1) a phenyl-benzylether of the formula I.a, I.b or I.c,

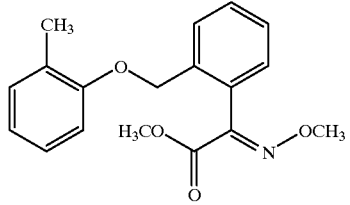

I.a

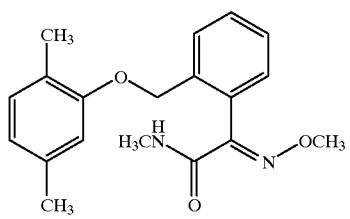

I.b

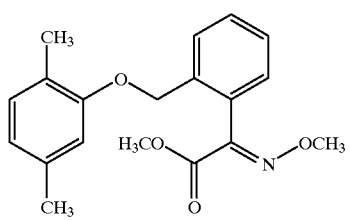

I.c or a.1) a carbamate of the formula I.d,

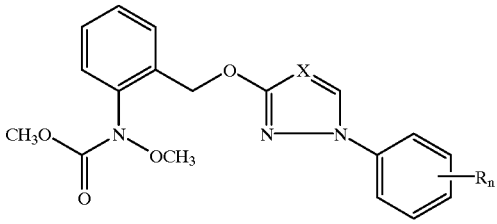

I.d where X is CH and N, n is 0, 1 or 2 and R is halogen, $C_1$–$C_4$-alkyl and $C_1$–$C_4$-haloalkyl, it being possible for the radicals R to be different when n is 2, and b) a dicarboximide-type fungicide (II)

in a synergistically active amount.

In particular the invention relates to compositions comprising a dicarboximide-type fungicide of the formulae II.a to II.d:

II.a: ethyl "(±)"-3-(3,5-dichlorophenyl)-5-methyl-2,4-dioxo-oxazolidine-5-carboxylate

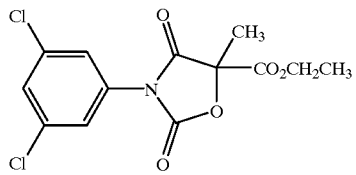

II.a or

II.b: 3-(3,5-dichlorophenyl)-N-isopropyl-2,4-dioxoimidazolidine-1-carboxamide

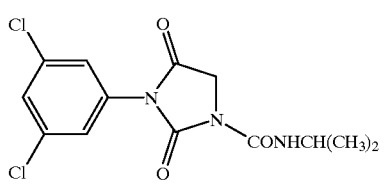

II.b or

II.c: N-(3,5-dichlorophenyl)-1,2-dimethylcyclopropane-1,2-dicarboximide

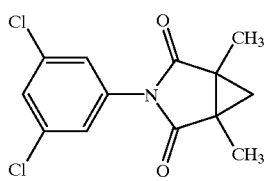

II.c or

II.d: (RS)-3-(3,5-dichlorophenyl)-5-ethenyl-5-methyl-1,3-oxazolidine-2,4-dione

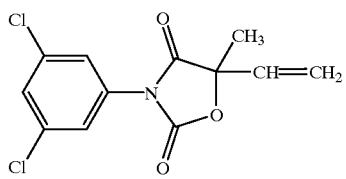

II.d

Moreover, the invention relates to methods of controlling harmful fungi with mixtures of the compounds I (I.a, I.b, I.c and I.d) and II (II.a, II.b, II.c and II.d).

The compounds of the formula I, their preparation and their action against harmful fungi have been disclosed in the literature (EP-A 253 213; EP-A 254 426; EP-A 398 692; EP-A 477 631; WO-A 93/15,046; WO-A 96/01,256; WO-A 96/01,258).

The compounds II, their preparation and their action against harmful fungi have also been disclosed:

II.a (common name: chlozolinate): CAS RN [84332-86-5], DE-A 29 06 574;

II.b (common name: iprodione): CAS RN [36734-19-7], U.S. Pat. No. 3,755,350;

II.c (common name: procymidone): CAS RN [32809-16-8], U.S. Pat. No. 3,903,090;

II.d (common name: vinclozoline): CAS RN [50471-44-8], DE-A 22 07 576].

It was an object of the present invention to provide mixtures which have an improved activity gainst harmful fungi combined with a reduced total amount of active ingredients applied (synergistic mixtures) with a view to reducing the rates of application and to improving the spectrum of action of the known compounds.

Accordingly, we have found that this object is achieved by the mixture defined at the outset. Moreover, we have found that better control of the harmful fungi is possible by applying the compound I and the compound II simultaneously together or separately or by applying the compound I and the compound II in succession than when the individual compounds are used.

In particular, the formula I.d represents carbamates in which the combination of the substituents corresponds to one line of the table which follows:

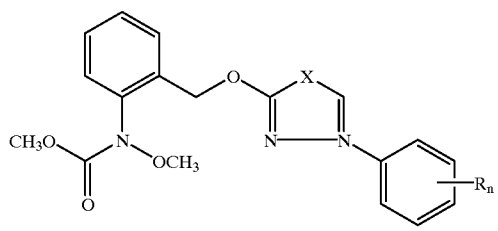

I.d

| No. | X | $R_n$ |
| --- | --- | --- |
| Id.1 | N | 2-F |
| Id.2 | N | 3-F |
| Id.3 | N | 4-F |
| Id.4 | N | 2-Cl |
| Id.5 | N | 3-Cl |
| Id.6 | N | 4-Cl |
| Id.7 | N | 2-Br |
| Id.8 | N | 3-Br |
| Id.9 | N | 4-Br |
| Id.10 | N | 2-$CH_3$ |
| Id.11 | N | 3-$CH_3$ |
| Id.12 | N | 4-$CH_3$ |
| Id.13 | N | 2-$CH_2CH_3$ |
| Id.14 | N | 3-$CH_2CH_3$ |
| Id.15 | N | 4-$CH_2CH_3$ |
| Id.16 | N | 2-$CH(CH_3)_2$ |
| Id.17 | N | 3-$CH(CH_3)_2$ |
| Id.18 | N | 4-$CH(CH_3)_2$ |
| Id.19 | N | 2-$CF_3$ |
| Id.20 | N | 3-$CF_3$ |
| Id.21 | N | 4-$CF_3$ |
| Id.22 | N | 2,4-$F_2$ |
| Id.23 | N | 2,4-$Cl_2$ |
| Id.24 | N | 3,4-$Cl_2$ |
| Id.25 | N | 2-Cl, 4-$CH_3$ |
| Id.26 | N | 3-Cl, 4-$CH_3$ |
| Id.27 | CH | 2-F |
| Id.28 | CH | 3-F |
| Id.29 | CH | 4-F |
| Id.30 | CH | 2-Cl |
| Id.31 | CH | 3-Cl |
| Id.32 | CH | 4-Cl |
| Id.33 | CH | 2-Br |
| Id.34 | CH | 3-Br |
| Id.35 | CH | 4-Br |
| Id.36 | CH | 2-$CH_3$ |
| Id.37 | CH | 3-$CH_3$ |
| Id.38 | CH | 4-$CH_3$ |
| Id.39 | CH | 2-$CH_2CH_3$ |
| Id.40 | CH | 3-$CH_2CH_3$ |
| Id.41 | CH | 4-$CH_2CH_3$ |
| Id.42 | CH | 2-$CH(CH_3)_2$ |
| Id.43 | CH | 3-$CH(CH_3)_2$ |

-continued

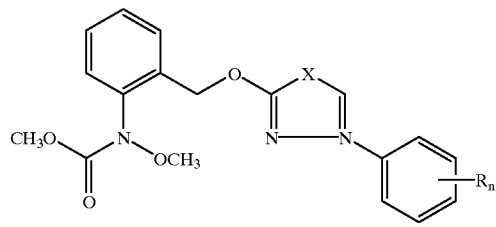

I.d.

| No. | X | $R_n$ |
| --- | --- | --- |
| Id.44 | CH | 4-$CH(CH_3)_2$ |
| Id.45 | CH | 2-$CF_3$ |
| Id.46 | CH | 3-$CF_3$ |
| Id.47 | CH | 4-$CF_3$ |
| Id.48 | CH | 2,4-$F_2$ |
| Id.49 | CH | 2,4-$Cl_2$ |
| Id.50 | CH | 3,4-$Cl_2$ |
| Id.51 | CH | 2-Cl, 4-$CH_3$ |
| Id.52 | CH | 3-Cl, 4-$CH_3$ |

The compounds I.12, I.23, I.32 and I.38 are especially preferred.

Due to the basic character, the compounds I and II are capable of forming adducts or salts with inorganic or organic acids or with metal ions.

Examples of inorganic acids are hydrohalic acids such as hydrofluoric acid, hydrochloric acid, hydrobromic acid and hydroiodic acid, sulfuric acid, phosphoric acid and nitric acid.

Suitable organic acids are, for example, formic acid, carbonic acid and alkanoic acids such as acetic acid, trifluoroacetic acid, trichloroacetic acid and propioric acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals having from 1 to 20 carbon atoms), arylsulfonic acids or -disulfonic acids (aromatic radicals such as phenyl and naphthyl which have attached to them one or two sulfo groups), alkylphosphonic acids (phosphonic acids having straight-chain or branched alkyl radicals of from 1 to 20 carbon atoms), arylphosphonic acids or -diphosphonic acids (aromatic radicals such as phenyl and naphthyl which have attached to them one or two phosphoric acid radicals), it being possible for the alkyl or aryl radicals to have attached to them further substituents, e.g. p-toluenesulfonic acid, salicylic acid, p-aminosalicylic acid, 2-phenoxybenzoic acid, 2-acetoxybenzoic acid etc.

Suitable metal ions are, in particular, the ions of the elements of the second main group, in particular calcium and magnesium, and of the third and fourth main group, in particular aluminum, tin and lead, and of the first to eighth subroup, in particular chromium, manganese, iron, cobalt, nickel, copper, zinc and others. Especially preferred are the metal ions of the elements of the sub-groups of the fourth period. The metals can in this case be in the various valences which they can assume.

When preparing the mixtures, it is preferred to employ the pure active ingredients I and II, with which further active ingredients against harmful fungi or other pests such as insects, arachnids or nematodes, or else herbicidal or growth-regulating active ingredients or fertilizers can be admixed, if so desired.

The mixtures of the compounds I and II, or the simultaneous joint or separate use of the compounds I and II, are distinguished by an outstanding activity against a broad spectrum of phytopathogenic fungi, in particular from the classes of the Ascomycetes, Deuteromycetes, Phycomycetes and Basidiomycetes. Some of them act systemically and can therefore be employed as foliar- and soil-acting fungicides.

They are especially important for controlling a large number of fungi in a variety of crop plants such as cotton, vegetable species (e.g. cucumbers, beans and curcubits), barley, grass, oats, coffee, maize, fruit species, rice, rye, soybeans, grapevine, wheat, ornamentals, sugar cane, and a variety of seeds.

They are particularly suitable for controlling the following phytopathogenic fungi: *Erysiphe graminis* (powdery mildew) on cereals, *Erysiphe cichoracearum* and *Sphaerotheca fuliginea* on curcubits, *Podosphaera leucotricha* on apples, *Uncinula necator* on grapevines, Puccinia species on cereals, Rhizoctonia species on cotton, rice and turf, Ustilago species on cereals and sugar cane, *Venturia inaequalis* (scab) on apples, Helminthosporium species on cereals and turf, *Septoria nodorum* on wheat, *Botrytis cinerea* (gray mold) on strawberries, vegetables, ornamentals and grapevines, Sclerotina species in rape and turf, *Cercospora arachidicola* on peanuts, *Pseudocercosporella herpotrichoides* on wheat and barley, *Pyricularia oryzae* on rice, *Phytophthora infestans* on potatoes and tomatoes, Pythium species in ornamentals, vegetables and turf, Pseudoperonospora species on cucurbits and hops, *Plasmopara viticola* on grapevines, Alternaria species on vegetables and fruit, and Fusarium and Verticillium species.

Furthermore, they can be used in the protection of materials (e.g. in the protection of wood), for example against *Paecilomyces variotii*.

The compounds I and II can be applied simultaneously together or separately or in succession, the sequence, in the case of separate application, generally not having any effect on the result of the control measures.

The compounds I and II are normally used in a weight ratio of from 20:1 to 0.1:2, preferably 10:1 to 0,1:1, in particular 5:1 to 0,2:1 (II:I).

The application rates of the mixtures according to the invention are, in the case of the compounds I, from 0.005 to 0.5 kg/ha, preferably 0.01 to 0.5 kg/ha, in particular 0.01 to 0.3 kg/ha, depending on the nature of the desired effect.

Correspondingly, in the case of the compound II, the application rates are from 0.1 to 10 kg/ha, preferably 0.5 to 5 kg/ha, in particular 1 to 4 kg/ha.

For seed treatment, the application rates of the mixture are generally from 0.001 to 100 g/kg seed, preferably 0.01 to 50 g/kg, in particular 0.01 to 10 g/kg.

If phytopathogenic harmful fungi are to be controlled, the separate or joint application of the compounds I and II or of the mixtures of the compounds I and II is effected by spraying or dusting the seeds, the plants or the soils before or after sowing of the plants, or before or after plant emergence.

The fungicidal synergistic mixtures according to the invention, or the compounds I and II, can be formulated for example in the form of ready-to-spray solutions, powders and suspensions or in the form of highly concentrated aqueous, oily or other suspensions, dispersions, emulsions, oil dispersions, pastes, dusts, materials for spreading or granules, and applied by spraying, atomizing, dusting, spreading or pouring. The use form depends on the intended purpose; in any case, it should guarantee as fine and uniform as possible a distribution of the mixture according to the invention.

The formulations are prepared in a manner known per se, e.g. by adding solvents and/or carriers. It is usual to admix inert additives, such as emulsifiers or dispersants, with the formulations.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, of alkyl- and alkylarylsulfonates, of alkyl, lauryl ether and fatty alcohol sulfates, and salts of sulfated hexa-, hepta- and octadecanols or fatty alcohol glycol ethers, condensates of sulfonated naphthalene and its derivatives with formaldehyde, condensates of naphthalene, or of the naphthalenesulfonic acids, with phenol and formaldehyde, polyoxyethylene octylphenyl ether, ethoxylated isooctyl-, octyl- or nonylphenol, alkylphenyl polyglycol ethers or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetate, sorbitol esters, ligninsulfite waste liquors or methylcellulose.

Powders, materials for spreading and dusts can be prepared by mixing or jointly grinding the compounds I or II or the mixture of the compounds I and II with a solid carrier.

Granules (e.g. coated granules, impregnated granules or homogeneous granules) are normally prepared by binding the active ingredient, or active ingredients, to a solid carrier.

Fillers or solid carriers are, for example, mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, and fertilizers such as ammonium sulfate, ammonium phosphate, ammonium nitrate, ureas, and products of vegetable origin such as cereal meal, tree bark meal, wood meal and nutshell meal, cellulose powders or other solid carriers.

The formulations generally comprise from 0.1 to 95% by weight, preferably 0.5 to 90% by weight, of one of the compounds I or II, or of the mixture of the compounds I and II. The active ingredients are employed in a purity of from 90% to 100%, preferably 95% to 100% (according to NMR or HPLC spectrum).

The compounds I or II, or the mixtures, or the corresponding formulations, are applied by treating the harmful fungi or the plants, seeds, soils, areas, materials or spaces to be kept free from them with a fungicidally active amount of the mixture, or of the compounds I and II in the case of separate application. Application can be effected before or after infection by the harmful fungi.

Examples of the synergistic action of the mixtures according to the invention against harmful fungi The fungicidal activity of the compounds and of the mixtures was demonstrated by the following experiments:

The active ingredients, separately or together, were formulated as a 10% emulsion in a mixture of 63% by weight of cyclohexanone and 27% by weight of an emulsifier, and diluted with water to give the desired concentration.

Action on *Botrytis cinerea* (Grey mould)

Paprika seedlings of the "Neusiedler Ideal Elite" variety and having 4–5 leaves were sprayed to runoff with aqueous formulations of the active ingredients. After the plants had dried they were sprayed with a conidial suspension of the fungus *Botrytis cinerea* and then kept for 5 days at 22–24° C. and at relative humidity of >90%. Assessment was visual.

Evaluation was carried out by determining the infected leaf areas in percent. These percentages were converted into efficacies. The expected efficacies of the mixtures of the active ingredients were determined using Colby's formula [R. S. Colby, Weeds 15, 20–22 (1967)] and compared with the observed efficacies.

Colby's formula:

$$E = x+y - x\cdot y/100$$

E expected efficacy, expressed in % of the untreated control, when using the mixture of the active ingredients A and B at concentrations of a and b x efficacy, expressed in % of the untreated control, when using active ingredient A at a concentration of a y efficacy, expressed in % of the untreated control, when using active ingredient B at a concentration of b The efficacy (W) was calculated as follows using Abbot's formula:

$$W = (1-\alpha)\cdot 100/\beta$$

α is the fungal infection of the treated plants in % and

β is the fungal infection of the untreated (control) plants in %

An efficacy of 0 means that the infection level of the treated plants corresponds to that of the untreated control plants; an efficacy of 100 means that the treated plants were not infected.

We claim:

1. A fungicidal composition comprising a) a carbamate of the formula I.d

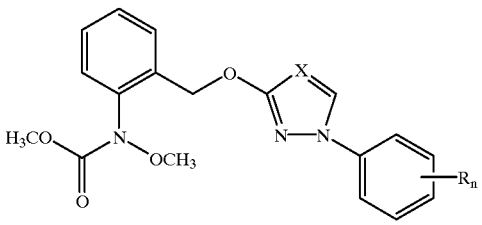

where X is CH, n is 0, 1 or 2 and R is halogen, $C_1$–$C_4$-alkyl or $C_1$–$C_4$-haloalkyl, it being possible for the radicals R to be different when n is 2, and b) a dicarboximide-type fungicide (II)

in a synergistically active amount, the weight ratio of the dicarboximide-type fungicide (II) to the carbamate of the formula I.d being of from 20:1 to 0.1:2.

2. The fungicidal composition defined in claim 1, wherein the dicarboximide-type fungicide (II) is selected from the group consisting of II.a: ethyl "(±)"-3-(3,5-dichlorophenyl)-5-methyl-2,4-dioxooxazolidine-5-carboxylate

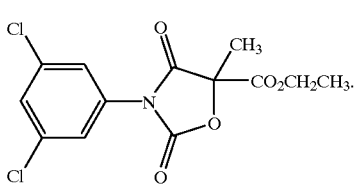

II.b: 3-(3,5-dichlorophenyl)-N-isopropyl-2,4-dioxoimidazolidine-1-carboxamide

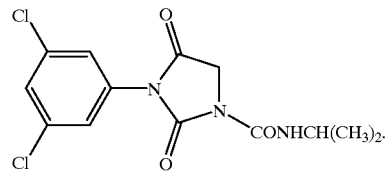

II.c: N-(3,5-dichlorophenyl)-1,2-dimethylcyclopropane-1,2-dicarboxamide

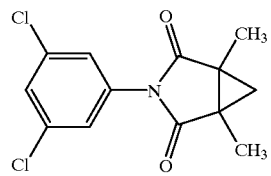

and

II.d: (RS)-3-(3,5-dichlorophenyl)-5-ethenyl-5-methyl-1,3-oxazolidine-2,4-dione

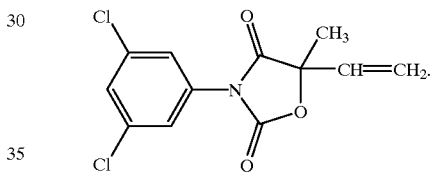

3. The fungicidal composition defined in claim 1, wherein the dicarboximide-type fungicide is (RS)-3-(3,5-dichlorophenyl)-5-ethenyl-5-methyl-1,3-oxazolidine-2,4-dione.

4. The fungicidal composition defined in claim 1, wherein R is halogen.

5. The fungicidal composition defined in claim 2, wherein R is halogen.

6. The fungicidal composition defined in claim 3, wherein R is halogen.

7. A method of controlling harmful fungi, which comprises treating the harmful fungi, their environment, or the plants, seeds, soils, areas, materials or spaces to be kept free from said fungi with a carbamate of the formula I.d as set forth in claim 1 and the dicarboximide-type fungicide (II) as set forth in claim 1 in synergistically active amounts.

8. The method of claim 7, wherein the carbamate of the formula I.d and the dicarboximide-type fungicide (II) are applied simultaneously together or separately or in succession.

9. The method of claim 7, wherein from 0.005 to 0.5 kg/ha of the carbamate of the formula I.d are applied.

10. The method of claim 7, wherein from 0.1 to 10 kg/ha of the dicarboximide-type fungicide (II) are applied.

11. The method of claim 7, wherein the dicarboximide-type fungicide is (RS)-3-(3,5-dichlorophenyl)-5-ethenyl-5-methyl-1,3-oxazolidine-2,4-dione.

12. The method of claim 7, wherein R is halogen.

13. The method of claim 11, wherein R is halogen.

* * * * *